United States Patent [19]

Snapp, Jr. et al.

[11] 3,954,742
[45] May 4, 1976

[54] DIOXANE TETRAETHER ESTERS

[75] Inventors: Thomas C. Snapp, Jr.; Alfred G. Robinson; Alden E. Blood, all of Longview, Tex.

[73] Assignee: Eastman Kodak Company, Rochester, N.Y.

[22] Filed: Aug. 16, 1974

[21] Appl. No.: 498,167

[52] U.S. Cl. .................. 260/240 J; 260/30.4 R; 260/340.6
[51] Int. Cl.² .................. C07D 319/12; C08K 5/15
[58] Field of Search .......... 260/340.6, 240 E, 240 J

[56] References Cited
UNITED STATES PATENTS
2,410,197  10/1946  Borglin ..................... 260/340.6 X OTHER PUBLICATIONS
Wagner et al., "Synthetic Organic Chemistry," (1953), J. Wiley and Sons, Inc., New York, pp. 480–483.

Primary Examiner—Anton H. Sutto
Attorney, Agent, or Firm—Edward R. Weber; Daniel B. Reece, III

[57] ABSTRACT

Para-dioxane esters of the formula

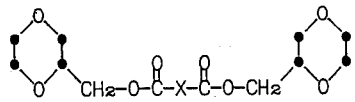

wherein X is an acrylic or cyclic aliphatic or aromatic moiety having from 1 to 8 carbon atoms are produced by esterification of 1,4-dioxanemethanol with a dicarboxylic acid of 3 to 10 carbon atoms or a corresponding acid anhydride. The novel esters are useful as plasticizers, viscosity improvers, and in waxes and polishes.

7 Claims, No Drawings

DIOXANE TETRAETHER ESTERS

This invention relates to a novel class of chemical compounds and more particularly to chemical compounds having the following structural formula:

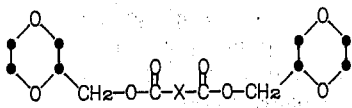

wherein X is an acyclic or cyclic aliphatic or aromatic moiety with 1 to 8 carbon atoms.

It is known that compatibility of organic compounds with resins, polymers and other organic compounds for commercial use is improved when the molecule contains both ester and ether linkages. It has now been found that 1,4-dioxanemethanol (para-dioxanemethanol) can be esterified with dicarboxylic acids or the corresponding acid anhydrides to yield molecules containing both ester and ether bonds that are useful as plasticizers, viscosity improvers and in waxes and polishes.

It is an object of this invention to provide tetraether esters of 1,4-dioxane useful as plasticizers for synthetic resins.

It is another object of this invention to provide tetraether esters of 1,4-dioxane useful in waxes and polishes.

Additional objects will be apparent from the following description and from the claims.

The compounds of this invention are a novel class of heterocyclic ether esters comprising a 1,4-dioxanemethanol nucleus which are useful as plasticizers for polyvinyl chloride resins, viscosity improvers in brake fluids and lubricants and as anti-slip agents and replacements for natural waxes in waxes and polishes. These compounds have the formula:

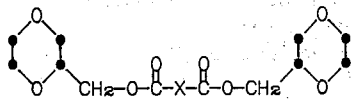

wherein X is an acyclic or cyclic aliphatic or aromatic moiety of 1 to 8 carbon atoms. Compounds of this type possess four ether and two ester linkages and can be considered tetraether esters. The esterification of 1,4-dioxanemethanol with a dicarboxylic acid of from 3 to 10 carbon atoms or the corresponding acid anhydride gives a new class of compounds having incorporated within a single molecule both ether and ester radicals. This combination of moieties within a given compound affords greater compatibility with resins, polymers, and other organic compounds. Unexpectedly, extremely good thermal and chemical stability is observed with these compounds even though they possess a multiplicity of oxygenated radicals (approximately 30–40 weight percent oxygen). This stability is quite unexpected as highly oxygenated compounds usually show poor thermal and chemical stability. These unexpected properties allow the compounds to be useful in many varied industrial applications. It has been discovered that these tetraether esters are very effective as plasticizers in polyvinyl chloride resins. In addition, they have been found to be useful as viscosity improvers in brake fluid, and lubricants and as anti-slip agents or replacements for natural waxes in waxes and polishes.

These novel cyclic tetraether esters are prepared from 1,4-dioxanemethanol by esterification. 1,4-Dioxanemethanol is a known chemical which may be prepared by numerous methods. See, for example, British Pat. 749,713 and U.S. Pat. No. 2,434,414. Esterfication to the cyclic tetraether ester is accomplished by reaction with a dicarboxylic acid having from 3 to 10 carbon atoms or the corresponding acid anhydride. The product is produced in good yields by either catalyzed or noncatalyzed reaction. A preferred method involves the noncatalyzed esterification. Reasons for the preference of the noncatalyzed method include (1) no catalyst residues, (2) good reaction rates, (3) elimination of potential side reactions resulting from the catalyst, and (4) improved economics.

Esterification of the 1,4-dioxanemethanol to the tetraether ester by an organic acid can be achieved in a catalyzed reaction with an azeotropic agent to facilitate removal of water produced during the esterification. Dicarboxylic acids suitable for the reaction include succinic, glutaric, adipic, malonic, suberic, o-phtalic, isophthalic, terephthalic and sebacic. The mole ratio of the reactant (diether alcohol to acid) should be from about 2.0:1.0 to about 4.0:1.0, respectively. A preferred reactant ratio is from about 2.2:1 to about 2.5:1. This provides good reaction rates and an economical process. A catalyst concentration of from about 0.01 to about 2.0 weight percent, based on the weight of the reactant in the reactor, should be maintained. A preferred catalyst concentration range is from about 0.1 to about 0.5 weight percent. Effective catalysts for this reaction include p-toluene-sulfonic acid, hydrochloric acid, sulfuric acid, organotin compounds and zinc chloride. Azeotropic agents used in this reaction are aliphatic and aromatic hydrocarbons such as benzene, toluene, hexane, xylene or cyclohexane. Reaction temperatures during the esterification should not exceed 225°C. since decomposition of the reactants can occur. A temperature range of from about 75° to about 225°C. is useful for the esterification reaction with a preferred range of from about 150° to about 200°C. to provide good reaction rates with high product yields. The reaction can be conducted at a greater than or below atmospheric pressure without detrimental effects to the product.

Esterification of the 1,4-dioxanemethanol to the tetraether ester by the acid anhydride method can be achieved by heating at from about 75°C. to about 225°C. in a noncatalyzed reaction. A preferred temperature range is from about 125°C. to about 175°C. Acid anhydrides suitable for the reaction include aliphatic and aromatic anhydrides having up to 10 carbon atoms such as the anhydrides of maleic, glutaric, suberic, sebacic, succinic and o-phthalic acids. Molar ratio of the reactants (diether alcohol to acid anhydride) can be from about 2.0:1.0 to about 4.0:1.0, respectively. A preferred mole ratio is from about 2.2:1 to about 2.5:1. This gives rapid reactions and high yields. If desired, the reaction can be catalyzed by the addition of 0.01 to 2.0 weight percent, based on the weight of the reactant, of catalyst. A preferred catalyst concentration is from about 0.1 to about 0.5 weight percent. Suitable catalysts for this reaction include sulfuric acid, organotin compounds (dibutyltin oxide, dibutyltin dilaurate, etc.), hydrochloric acid, zinc chloride, p-toluenesulfonic acid, pyridine, triethylamine, and N,N-dimethyl aniline. The reaction can be conducted at a greater than or below atmospheric pressure without detrimental effects to the product.

The process of the invention is illustrated in greater detail by the following examples which are all conducted at atmospheric pressure. It will be understood that these examples are not intended to limit the invention in any way and obvious modifications will occur to those skilled in the art.

EXAMPLE 1

This example demonstrates the synthesis of a tetraether adipate. Into a 2-liter flask with an attached Dean-Stark apparatus are placed 365 grams (2.5 moles) adipic acid, 590 grams (5.0 moles) 1,4-dioxanemethanol, 200 milliliters xylene, and 0.7 gram dibutyltin oxide catalyst. This mixture is refluxed until 90 milliliters of water is collected in the Dean-Stark trap. The reaction product is heated at 125°C. and 10 mm. mercury pressure to remove xylene. The residue is the tetraetherester product which is a solid melting at 58°–60°C. Recrystallization from ethanol gives an 81 percent yield. Molecular weight and saponification equivalent analyses verify formation of the desired bis-1,4-dioxane-methanol adipate.

EXAMPLE 2

This example demonstrates the synthesis of a tetraether diester with an aromtic anhydride. Into a 2-liter flask with an attached Dean-Stark apparatus are placed 148 grams (1 mole) of phthalic anhydride, 295 grams (2.5 moles) 1,4-dioxanemethanol, 100 milliliters of benzene and 0.1 gram of p-toluenesulfonic acid catalyst. This mixture is refluxed at 200°C. until 18 milliliters of water collects in the Dean-Stark trap. The reaction product is heated at 100°C. and 10 millimeters mercury pressure to remove benzene and excess 1,4-dioxanemethanol. The residue solidifies on cooling and is recrystallized from either an ethanol or ethanol-water mixture to give an 85 percent yield to the tetraether diester. Molecular weight, saponification equivalent and infrared spectroscopy analyses confirm the synthesis of the novel tetraether ester, bis-1,4-dioxanemethanol phthalate.

EXAMPLE 3

Following the procedure of Example 2, a mixture of 166 grams (1 mole) of isophthalic acid, 295 grams (2.5 moles) of 1,4-dioxanemethanol, 100 milliliters of benzene and 0.1 gram of p-toluenesulfonic acid catalyst gives an 86 percent yield of the white, waxy bis-1,4-dioxanemethanol isophthalate.

EXAMPLE 4

Following the procedure of Example 2, a mixture of 98 grams (1 mole) of maleic anhydride, 354 grams (3.0 moles) of 1,4-dioxanemethanol and 50 milliliters of benzene affords an 82 percent yield of bis-1,4-dioxanemethanol maleate.

EXAMPLE 5

Following the procedure of Example 2, a mixture of 87.1 grams (0.5 mole) of sebacic acid, 146.5 grams (1.25 moles) of 1,4-dioxanemethanol, 50 milliliters of toluene and 0.2 gram of dibutyltin dilaurate catalyst yields a waxy product in 87 percent yield which is recrystallized from an isopropanol-water mixture to give the colorless bis-1,4-dioxanemethanol sebacate.

EXAMPLE 6

Following the procedure of Example 2, a mixture of 172 grams (1.0 mole) of cyclohexane dicarboxylic acid, 265.5 grams (2.25 moles) of 1,4-dioxanemethanol, 75 milliliters of xylene and 0.3 gram of dibutyltin oxide catalyst yields a gray waxy product in 91 percent yield. Recrystallization from an ethanol-water mixture gives the colorless bis-1,4-dioxanemethanol cyclohexanedicarboxylate.

The invention has been described in detail with particular reference to preferred embodiments thereof, but it will be understood that variations and modifications can be effected within the spirit and scope of the invention as described hereinabove.

We claim:

1. A compound having the formula:

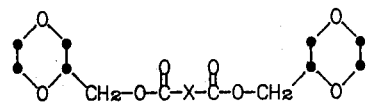

wherein X is an acyclic or alicyclic hydrocarbon or aromatic moiety having 1 to 8 carbon atoms.

2. The tetraether ester compound of claim 1 wherein X is $-\!\!+\!\!CH_2\!\!+\!\!_4$.

3. The tetraether ester compound of claim 1 wherein X is 1,3-phenylene.

4. The tetraether ester compound of claim 1 wherein X is $-\!\!+\!\!CH_2\!\!+\!\!_8$.

5. The tetraether ester compound of claim 1 wherein X is $-CH\!=\!CH-$.

6. The tetraether ester compound of claim 1 wherein X is ortho (1,2-) phenylene.

7. The tetraether ester compound of Claim 1 wherein X is

* * * * *